US00PP08241P

United States Patent [19]

van der Knapp

[11] Patent Number: Plant 8,241

[45] Date of Patent: May 25, 1993

[54] CHRYSANTHEMUM PLANT — FUNRISE CULTIVAR

[75] Inventor: Jacques C. M. van der Knapp, De Lier, Netherlands

[73] Assignee: Fides Beheer B.V., De Lier, Netherlands

[21] Appl. No.: 719,465

[22] Filed: Jun. 24, 1991

[51] Int. Cl.[5] ..... A01H 5/00

[52] U.S. Cl. ..... Plt./82.4

[58] Field of Search ..... Plt./74, 74.1, 82.4, Plt./76, 80

[56] References Cited

U.S. PATENT DOCUMENTS 4,616,099 10/1986 Sparkes ..... 47/58

OTHER PUBLICATIONS

Broertjes et al. 1980. "A Mutant of a Mutant of a Mutant of a . . . Irradiation of Progressive Radiation-Induced Mutants in a Mutation Breeding Programme with *Chrysanthemum morifolium*", Euphytica 29:525-530.

Gosling, S. ed 1979. "The Chrysanthemum Manual", National Chrysanthemum Society, London, England, pp. 329-336.

Broertjes et al. 1978. "Application of Mutation Breeding Methods in the Improvement of Vegetatively Propagated Crops", Elsevier Pub. Co., New York, pp. 162-175.

Searle, et al. 1968. "Chrysanthemums the Year Round". Blanford Press, London. pp. 26-29, 320-327.

Broertjes, 1966. "Mutation Breeding of Chrysanthemums", Euphytica 15:156-162.

Chan et al. 1966. "Chrysanthemum and Rose Mutations Induced by X-Rays", Am. Soc. Hort. Sci. vol. 88:613-620.

Dowrick et al. 1966. "The Induction of Mutations in Chrysanthemum Using X- and Gamma Radiation". Euphytica 15:204-210.

*Primary Examiner*—Howard J. Locker

*Attorney, Agent, or Firm*—Burns, Doane, Swecker & Mathis

[57] ABSTRACT

A new and distinct cultivar of Chrysanthemum plant named Funrise is provided. The new cultivar was the result of a mutation induced by controlled irradiation with x-rays and can be readily distinguished from the parent Funshine cultivar (U.S. Ser. No. 719,461, filed concurrently herewith). More specifically, the new cultivar forms attractive relatively small bicolored flowers wherein the petals are red-purple instead of white as the Funshine cultivar and the disc florets particularly towards the center bear a slightly more intense red coloration on the distal ends (as illustrated) than the Funshine cultivar. The inflorescence tends to be pyramidal in configuration. The response period of the flowers is approximately seven and one-half weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Funrise.

The new cultivar is a mutation which was induced in a plant of the Funshine cultivar (U.S. Ser. No. 719,461, filed concurrently herewith) by irradiation with x-rays at a level of 1750 rads. The discovery of the new cultivar was made at De Lier, The Netherlands, during June, 1987. The discovery resulted in the identification of a single plant of the new cultivar.

It was found that the new cultivar of the present invention:

(a) exhibits attractive relatively small anemone flowers having an overall diameter of approximately 40 mm. wherein the petals are red-purple instead of white as the Funshine cultivar and the disc florets particularly towards the center bear a slightly more intense red coloration on the distal ends than the Funshine cultivar, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

Asexual reproduction of the new cultivar by cuttings performed at De Lier, The Netherlands, in a controlled environment has demonstrated that the characteristics of the new cultivar as herein disclosed are firmly fixed and are retained through successive generations of asexual propagation.

Funrise has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Improved Funshine cultivar (U.S. Ser. No. 719,464, filed concurrently herewith), the Improved Funshine cultivar is found to exhibit white petals and red coloration at the distal ends of the disc florets which is stronger and more intense than that of the Funshine cultivar. When the new cultivar of the present invention is compared to the Funbeam cultivar (U.S. Ser. No. 719,463, filed concurrently herewith), it is noted that the Funbeam cultivar exhibits red-purple petals which tend to be slightly lighter than those of the Funrise cultivar and tends to exhibit a slightly more intense light-red coloration on the distal ends of the disc florets than the Funshine cultivar. When the new cultivar of the present invention is compared to the Funset cultivar (U.S. Ser. No. 719,462, filed concurrently herewith), it is noted that the Funset cultivar exhibits very light-red petals and orange-red coloration on the distal ends of the disc florets. When the new cultivar of the present invention is compared to the Funglow cultivar (U.S. Ser. No. 720,211, filed concurrently herewith), it is noted that the Funglow cultivar exhibits yellow petals and greyed-purple coloration on the distal ends of the disc florets.

Plants of the Funrise cultivar can be readily distinguished from those of the parent Funshine cultivar by the following combination of characteristics which were obtained during recent observations:

| | Parent FUNSHINE Cultivar | FUNRISE Cultivar |
|---|---|---|
| Color of ray florets | White Group 155D | Red-Purple 62C |
| Color of disc florets | Red Group 51B | Red Group 54A |
| Flower diameter | Approximately 45 mm. | Approximately 40 mm. |
| Flower disc diameter | Approximately 30 mm. | Approximately 20 mm. |
| Foliage length | Approximately 80 mm. | Approximately 65 mm. |
| Foliage width | Approximately 60 mm. | Approximately 55 mm. |

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during December, 1990. The plants described were grown under standard greenhouse conditions which approximate those commonly utilized for the production of cut mums.

Classification:

*Botanical.*—*Chrysanthemum morifolium* Ramat., cv. Funrise.

*Commercial.*—Cut anemone spray.

Inflorescence

A. Capitulum:

*Form.*—Pyramidal.

*Type.*—Anemone.

*Diameter across face.*—Approximately 40 mm. on average.

*Diameter of flower center.*—Approximately 20 mm. on average.

B. Corrolla of ray and disc florets:

*Color (General tonality from a distance of three meters).*—Red-purple with darker center.

*Color ray florets (top surface).*—Red-purple, Red-purple Group 62C.

*Color disc florets.*—Red, Red Group 54A.

C. Reproductive organs:

*Androecium.*—Not present.

*Gynoecium.*—Present in both ray and disc florets.

Plant

A. General appearance:

*Height.*—Approximately 90 cm. on average.

B. Foliage:

*Color (upper surface).*—Yellow-Green group 147A.

*Color (under surface).*—Yellow-Green group 147B.

*Size.*—Approximately 80 mm. in length, and approximately 60 mm. in width.

I claim:

1. A new and distinct cultivar of Chrysanthemum plant named Funrise, substantially as herein shown and described, which:

(a) exhibits attractive relatively small anemone flowers having an overall diameter of approximately 40 mm. wherein the petals are red-purple instead of white as the Funshine cultivar and the disc florets particularly towards the center bear a slightly more intense red coloration on the distal ends than the Funshine cultivar, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

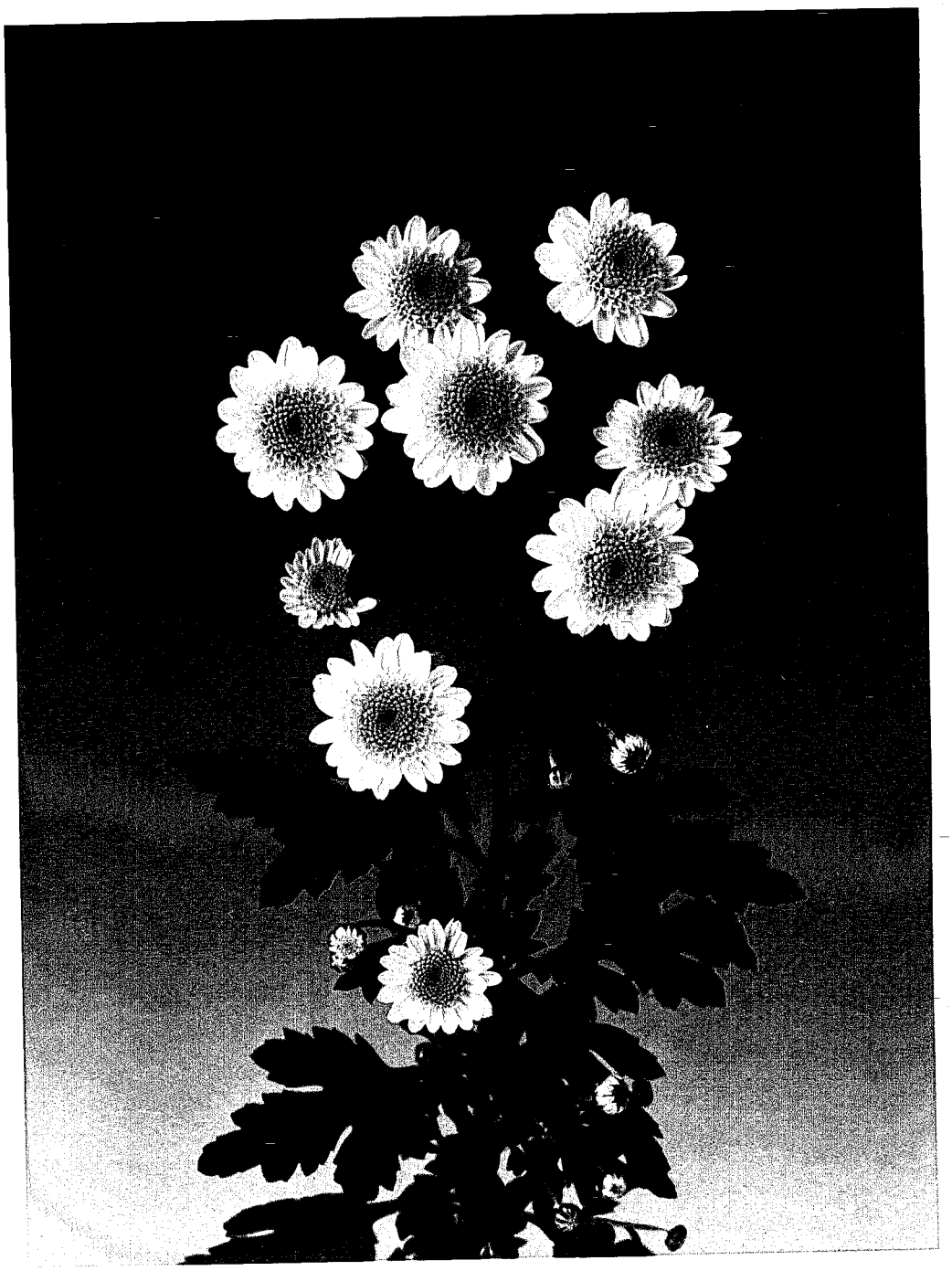

* * * * *